(12) United States Patent
Seaver et al.

(10) Patent No.: US 6,803,208 B2
(45) Date of Patent: Oct. 12, 2004

(54) AUTOMATED EPIFLUORESCENCE MICROSCOPY FOR DETECTION OF BACTERIAL CONTAMINATION IN PLATELETS

(75) Inventors: Mark Seaver, Burtonsville, MD (US); James C. Crookston, McLean, VA (US); Stephen J. Wagner, Columbia, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 458 days.

(21) Appl. No.: 09/916,272

(22) Filed: Jul. 30, 2001

(65) Prior Publication Data

US 2003/0022270 A1 Jan. 30, 2003

(51) Int. Cl.$^7$ ................................................. C12Q 1/04
(52) U.S. Cl. ........................................... 435/34; 435/29
(58) Field of Search ............................... 435/34, 2, 29, 435/243, 259, 287.4; 424/532; 210/782, 789, 806

(56) References Cited

U.S. PATENT DOCUMENTS

| | | | |
|---|---|---|---|
| 4,410,630 A | * | 10/1983 | Zierdt ..................... 435/297.2 |
| 4,693,972 A | * | 9/1987 | Mansour et al. .............. 435/34 |
| 4,717,660 A | | 1/1988 | Schulte |
| 5,545,535 A | | 8/1996 | Roth et al. |
| 5,548,661 A | | 8/1996 | Price et al. |
| 5,556,790 A | | 9/1996 | Pettit |
| 5,798,221 A | | 8/1998 | AEgidius |
| 5,828,716 A | | 10/1998 | Bisconte de Saint Julien |
| 5,858,697 A | | 1/1999 | Groner et al. |
| 5,891,394 A | | 4/1999 | Drocourt et al. |
| 5,976,892 A | | 11/1999 | Bisconte |
| 6,122,396 A | | 9/2000 | King et al. |
| 6,174,698 B1 | | 1/2001 | Miller |
| 6,197,593 B1 | | 3/2001 | Deka et al. |
| 6,215,586 B1 | | 4/2001 | Clark |
| 6,228,652 B1 | | 5/2001 | Rodriguez et al. |

FOREIGN PATENT DOCUMENTS

EP  0 333 560 B1  4/1994

OTHER PUBLICATIONS

Richard P. Haughland & Joanne L. Bratten, Bacteria Counting Kit, Handbook of Fluorescent Probes and Research Chemicals 6th ed., found at http://www.probes.com Dec. 22, 1996, p. 375, published by Molecular Probes, Inc..

* cited by examiner

*Primary Examiner*—Ralph Gitomer
(74) *Attorney, Agent, or Firm*—John J. Karasek; Stephen T. Hunnius

(57) ABSTRACT

A method for determining the presence of bacteria in a platelet or red blood cell sample is disclosed. The method includes the steps of: lysing a substantial portion of the platelets or red blood cells; staining the bacteria using a membrane permeable nucleic acid stain; filtering the sample using a membrane filter with a suitable pore size so that a material containing the stained bacteria is retained on the membrane filter; and analyzing the material retained on the membrane filter using epifluorescence microscopy and/or digital image acquisition and analysis to determine the presence of bacteria in the sample. The method allows the detection of bacterial contamination in platelets or red blood cells at clinically significant levels in a relatively short period of time.

25 Claims, No Drawings

AUTOMATED EPIFLUORESCENCE MICROSCOPY FOR DETECTION OF BACTERIAL CONTAMINATION IN PLATELETS

BACKGROUND OF THE INVENTION

1. Field of the Invention

The present invention relates to a method of detecting bacterial contamination in platelets or red blood cells using automated epifluorescence microscopy.

2. Description of the Prior Art

Bacterial contamination in blood platelets occurs in about 1 in every 1000–2000 units. Nationwide, this produces at least 150 cases per year of severe illness and occasional deaths. Because of this, there is a need for a rapid, inexpensive method which can detect and count bacteria in platelets at concentrations below $10^5$ colony forming units (CFU)/ml. To this date, only culturing, polymerase chain reaction (PCR), and fluorescence conjugated antibiotics are consistently able to detect bacteria at concentrations below $10^5$ colony forming units (CFU)/ml. The automated culture method, which can detect a single organism, requires at least 24 hrs to make a determination. PCR works well down to $10^4$ CFU/ml but is labor intensive and can take several hours. The use of fluorescent antibiotics has only been tested on one bacterial strain.

Fluorescent dyes are routinely used in microbiology to detect proteins, amino acids, nucleic acids, and whole cells, as well as biological activity in a wide variety of systems. U.S. Pat. No. 4,693,972 to Mansour et al. discloses a method for detecting microorganisms in blood based on lysis of the blood components and staining the microorganisms in the blood with the fluorescent dye ethidium bromide. However, because ethidium bromide is not membrane-permeable, it does not stain live bacteria. Thus, the sample preparation requires an extra step of permeablizing the bacterial cell membrane without disrupting the cell if detection of bacterial contamination is desired. Mansour et al. use a cytometer to count the microorganism cells and a centrifuge to concentrate microorganisms in the sample before it is analyzed. Cytometers are expensive and their operation is labor intensive.

U.S. Pat. No. 5,798,221 to AEgidius uses ethidium bromide to stain bacteria in a milk sample followed by counting the bacterial cells by passing the sample through a cytometer. Due to the poor permeability of ethidium bromide into bacterial cells, a combination of a chelating agent and a detergent is required in order to digest protein particles and enhance the staining of bacterial cells with ethidium bromide.

U.S. Pat. No. 4,717,660 to Schulte discloses a method for detecting microorganisms in a blood sample involving: a) selectively staining the microorganisms in the blood sample using a fluorochrome dye such as ethidium bromide or acridine orange and a staining buffer, b) centrifuging the sample with a centrifuge tube provided with a float, and c) detecting the fluorescence using flow cytometry. Again, using flow cytometry is expensive and labor-intensive. In addition, a staining buffer is required to enable the staining of microorganisms using ethidium bromide. Acridine Orange also readily stains other particles including platelets. The method of Schulte has difficulty in detecting bacterial contamination in platelets at concentrations below $10^5$ CFU/ml.

U.S. Pat. No. 5,828,716 to Bisconte de Saint Julien discloses an automated method for analyzing particles at magnifications below 100× magnification. At such a low magnification, the size and shape information critical to distinguishing bacteria from other fluorescent particles is lost.

U.S. Pat. No. 5,545,535 to Roth et al. discloses a method of analyzing a sample thought to contain bacteria using an aqueous solution comprising one or more fluorescent dyes. Roth et al. further discloses several generic methods for detecting the stained bacteria including the use of epifluorescence microscopy coupled with digital image acquisition. Roth et al. also exemplifies the use of filtration to concentrate the bacteria-containing samples. However, the lowest bacterial concentration detected in Roth et al. is $5 \times 10^5$ CFU/ml due to the limitations of its methods.

Therefore, it is an objective of certain embodiments of the present invention to provide a method for detecting bacteria which can detect bacteria at concentrations as low as $3.0 \times 10^3$ CFU/ml, which is below the clinically significant level.

It is another objective of certain embodiments of the present invention to provide a method for detecting bacteria which does not require a culturing step so as to provide rapid detection.

It is a further objective of certain embodiments of the present invention to provide a method for detecting bacteria in platelet-containing sample which is not labor intensive and has the capability of distinguishing a variety of sources of fluorescence from that of bacteria by taking advantage of digital image acquisition technology.

SUMMARY OF THE INVENTION

In a first aspect, the present invention relates to a method for ascertaining the presence of bacteria in a sample containing platelets or red blood cells comprising the steps of: lysing a substantial portion of the platelets or red blood cells in the sample; staining at least a substantial portion of the bacteria using a membrane-permeable nucleic acid stain; filtering the sample using a membrane filter to obtain a material containing substantially all of the stained bacteria; and analyzing the filtered material using epifluorescence microscopy to ascertain the presence of the bacteria in the sample.

In a second aspect, the present invention relates to a method for determining the concentration of bacteria in a sample containing platelets or red blood cells comprising the steps of: lysing a substantial portion of the platelets or red blood cells without destroying a substantial amount of the bacteria in the sample; staining the bacteria using a membrane-permeable nucleic acid stain; filtering the sample using a membrane filter to obtain a material containing substantially all of the stained bacteria; and analyzing the material using epifluorescence microscopy and digital image acquisition and analysis to determine the concentration of the bacteria in the sample.

DETAILED DESCRIPTION OF THE PREFERRED EMBODIMENTS

In a first aspect, the present invention relates to a method for ascertaining the presence of bacteria in a sample containing platelets or red blood cells comprising the steps of: lysing a substantial portion of the platelets or red blood cells in the sample; staining at least a substantial portion of the bacteria using a membrane-permeable nucleic acid stain; filtering the sample using a membrane filter to obtain a material containing substantially all of the stained bacteria; and analyzing the filtered material using epifluorescence microscopy to ascertain the presence of the bacteria in the sample.

The presence of bacteria in a platelet or red blood cell-containing sample can be defined as a sample which is not substantially free of bacteria. Alternatively, the presence of bacteria in a platelet or red blood cell-containing sample can be defined as the sample having a bacterial concentration higher than a clinically significant level, such as $1\times10^5$ CFU/ml. More preferably, the presence of bacteria in a platelet or red blood cell-containing sample can be defined as the sample having a bacterial concentration higher than a threshold level such as $3.0\times10^3$ CFU/ml.

In the method of the present invention, a platelet or red blood cell-containing sample which may possibly be contaminated with bacteria is treated with an effective amount of a lytic agent for a sufficient period of time to lyse a substantial portion of platelets or red blood cells in the sample. The lysis step may also lyse other proteins which may be present in the sample. After the lysis step, the sample is exposed to a membrane-permeable nucleic acid stain for a sufficient period of time to stain the nucleic acids in bacteria contained in the sample. Then the sample is filtered through a membrane filter with a suitable pore size to concentrate the sample into a material on the membrane filter. The pore size of the membrane filter is chosen such that a substantial portion of the lysed platelets or red blood cells and other proteins readily pass through the membrane filter whereas substantially all the stained bacteria in the sample are retained in the material on the membrane filter.

The membrane filter is then mounted onto a microscope and epifluorescence microscopy is employed to ascertain the presence of bacteria in the sample by determining the level of fluorescence in the sample. Fluorescence in the sample is primarily due to the presence of stained bacteria. Thus, the presence of localized fluorescence in the sample can indicate the presence of bacteria in the sample.

Preferably, after the filtration step, the membrane filter is sandwiched between two microscope slides to maximize the flatness of the membrane filter before being mounted onto a microscope for epifluorescence detection.

In a more preferred method in accordance with the present invention, a determination of whether the concentration of bacteria present in the platelet-containing sample exceeds a threshold level is made. In the preferred method, the step of lysing the platelets is carried out without destroying a substantial portion of the bacteria present in the sample. Also, sufficient membrane-permeable nucleic acid stain is employed to stain substantially all of the bacteria contained in the sample. Epifluorescence microscopy is used to acquire epifluorescent images. The images are then analyzed to determine the existence and quantity of the bacteria in the sample. The digital image acquisition and analysis increases the sample size of the epifluorescent microscopy via the acquisition and analysis of a plurality of images of different locations on the microscope slide. Also, the purpose of the digital image analysis is to distinguish fluorescence from bacteria from fluorescence from other materials, which may be present in the sample to thereby increase the selectivity of the method. Preferably, the analysis of the images is carried out using an analysis program relying on one or more of size, shape, and changes in brightness to distinguish between bacteria and other fluorescent particles.

Preferably, after analyzing the acquired images, the analysis program gives a count, which is normally a measure of the presence of the bacteria in the sample. Preferably, the count measured is compared with a threshold count to determine the presence of the bacteria in the sample. Typically, the threshold count may be equipment-related and may be calibrated using control samples.

When automated epifluorescence microscopy is coupled with digital image acquisition and analysis, large areas of a microscope slide can be interrogated and particle size, shape, position, and fluorescence intensity can be measured in seconds to minutes. One important factor in the detection of bacteria in platelets is the ability of distinguishing bacteria cells from a variety of other sources of fluorescence that are similar in size to the bacteria.

Preferably more than one digital epifluorescent image is acquired and analyzed for each sample. More preferably, 10–1000 images are acquired and analyzed for each sample. Most preferably, about 50–200 images are acquired and analyzed for each sample.

In a preferred embodiment of the present invention, the method is used to detect the presence of bacterial contamination in platelet suspensions, which are commonly prepared, stored and used in blood banks, hospitals, and clinics.

In another preferred embodiment of the present invention, the method is used to detect the presence of bacterial contamination in human blood, which is also commonly collected, stored and used in blood collecting vehicles, blood banks, clinical settings for transfusion and other appropriate purposes.

In a third preferred embodiment of the present invention, the method is used to detect the presence of bacterial contamination in red blood cell suspensions, which are commonly prepared, stored and used in blood banks, hospitals, and clinics.

Preferably, an effective amount of the lytic agent ranges from 0.5% to 20% by volume of the platelet suspension. More preferably, the effective amount of the lytic agent is about 4–10% by volume of the platelet suspension.

Preferably, an effective amount of the lytic agent ranges from 0.5% to 20% by volume of the red blood cell suspension. More preferably, the effective amount of the lytic agent is about 4–10% by volume of the red blood cell suspension.

Preferably, the lytic agent is a material that preferentially lyses platelets or red blood cells without destroying a substantial portion of the bacteria present in the sample or interfering with the membrane-permeable nucleic acid staining. More preferably, the lytic agent is a detergent. Most preferably, the lytic agent is Triton X-100 (trademark of Rohm and Haas Co. for octyl phenoxy polyethocyethanol).

Preferably, a first sufficient period of time for the lysis step ranges from 5 minutes to 30 minutes. More preferably, the lysis is carried out for about 10–20 minutes, and most preferably, the lysis step is about 15 minutes. Lysis time may depend on the specific lytic agent employed and on sample size, among other factors.

Suitable lysis temperatures may depend on the particular lytic agent used. Preferably, lysis is carried out at a temperature between 10° C. and 45° C. More preferably, lysis is carried out at about 37° C., when Triton X-100 is used as the lytic agent.

For a red blood cell or platelet-containing sample, preferably, enough red blood cells or platelets are lysed so that the when the sample is filtered through the membrane filter, the sample will not plug the filter and the fluorescence emitted by the unlysed platelets does not interfere significantly with the measurement results. Preferably, at least about 80% of the red blood cells or platelets are lysed. More preferably, during the lysing step, more than 90% of the red blood cells or platelets are lysed. Even more preferably, during the lysing step, more than 99% of the red blood cells or platelets are lysed. Most preferably, during the lysing step, more than 99.9% of the red blood cells or platelets are lysed.

Preferably, during the lysing step, a substantial amount of the bacteria in the sample remains intact so that the lysis does not significantly affect the measurement of the bacteria. More preferably, during the lysing step, the amount of the bacteria destroyed is within the experimental error of the method of the present invention. Even more preferably, less than 20% of the bacteria in the sample are destroyed during the lysis step. Most preferably, less than 10% of the bacteria in the sample are destroyed during the lysis step.

Preferably, during the filtration through a membrane filter, more than 90% of the lysed platelets or red blood cells pass through the filter, whereas more than 90% of the stained bacteria are retained in a material on the filter. More preferably, during the filtration through the membrane filter, more than 99% of the lysed platelets or red blood cells pass through the filter, whereas more than 95% of the stained bacteria are retained in the material on the filter.

The staining step may be carried out over a period of 1–30 minutes, preferably 1–15 minutes, and most preferably 10–15 minutes. Staining time may depend on a number of factors such as the specific stain used, sample size, etc.

Preferably, the membrane filter is a black membrane filter which does not emit fluorescence. More preferably, the membrane filter has a size of 25 mm so that it can fit between the typical microscope slides.

The membrane filter used in the step of filtering the sample has a suitable pore size to retain the stained bacteria on the filter and pass lysed platelets or red blood cells through the filter. More preferably, the pore size of the membrane filter is not less than 0.2 $\mu$m and no more than the diameter of the bacterial cell. Most preferably, the pore size of the membrane filter is about 0.4 $\mu$m. If the pore size of the membrane filter is too small, the membrane filter will be plugged quickly. Therefore, only a small volume of platelet or red blood cell suspension will be filtered off and the sensitivity of the method is reduced. If the pore size of the membrane filter is too large, a substantial portion of the bacteria cells will pass through the membrane filter and this will provide inaccurate measurements.

Typically, each time, only a certain volume of sample is needed to determine the bacterial contamination. Too large of a sample may plug the membrane filter. Too small of a sample may reduce the sensitivity of the method. Preferably, 10:1 to 400:1 of undiluted platelet or red blood cell suspension is filtered through the membrane filter each time. More preferably, about 200:1 of undiluted platelet or red blood cell suspension is filtered through the membrane filter each time. One significant advantage of the present invention is that the method can be successfully performed to give either a quantitative or qualitative analysis using relatively small sample volumes. Another significant advantage of the method of the present invention is that the cycle time for carrying out measurements is relatively short.

Preferably, the epifluorescence microscopy is carried out at a magnification of 100 times to 1000 times. More preferably, the epifluorescence microscopy is carried out at a magnification of about 200 times. If the magnification is too low, the size and shape information of the stained bacteria, which is important in distinguishing the bacteria from other fluorescent particles, may not be determinable, if the magnification is too high, the interrogation area of the membrane filter during each imaging will be small. Therefore, more images will be needed for the method to achieve an acceptable accuracy and reliability and the time duration for measurement will be increased.

Preferably, the epifluorescence microscopy is carried out using an automated epifluorescence microscope with automated digital image acquisition. More preferably, the epifluorescence microscope has an automated stage control for automated image acquisition and analysis. This reduces personnel needs and the likelihood of human error. In addition, the automated epifluorescence microscope preferably has several digital filters to separate bacterial images from the background and other particles that also fluoresce to facilitate the image analysis process.

The preferred membrane-permeable stain should provide good differentiation between fluorescence from the stained nucleic acids in the bacteria and fluorescence from stain which may be bound to other elements of the sample, such as platelets, red blood cells or serum proteins so that the method of the present invention can achieve a good sensitivity. More preferably, the membrane-permeable stain used in the present invention is a SYTO dye (SYTO is a trademark of Molecular Probes. Inc. for cell-permeant 6nucleic acid stains that show a large fluorescence enhancement upon binding nucleic acids) such as SYTO 40 blue, SYTO 41 blue, SYTO 42 blue, SYTO 43 blue, SYTO 44 blue, SYTO 45 blue, SYTO 13 green, SYTO 16 green, SYTO 24 green, SYTO 21 green, SYTO 23 green, SYTO 12 green, SYTO 11 green, SYTO 20 green, SYTO 22 green, SYTO 15 green, SYTO 14 green, SYTO 25 green, SYTO 81 orange, SYTO 80 orange, SYTO 82 orange, SYTO 83 orange, SYTO 84 orange, SYTO 85 orange, SYTO Orange, SYTO 64 red, SYTO 17 red, SYTO 59 red, SYTO 61 red, SYTO 62 red, SYTO 60 red, or SYTO 63 red. Most preferably, the membrane permeable stain used in the present invention is SYTO 13.

Preferably, the membrane filter is completely dried after filtration of the lysed platelets or lysed red blood cells and before being sandwiched between two microscope slides in order to reduce the fluorescence quenching rate, which in turn reduces the exposure time for each image.

Measurement speed in the method of the present invention may be traded off against sensitivity for particular applications. Acquiring and analyzing more images may increase the sensitivity of the method while reducing the measurement speed, or vice versa. Typically, in the method of the present invention, about 100 images may be acquired and analyzed in less than 10 minutes to achieve a typical detection limit of $3.0 \times 10^3$ CFU/ml. Acquiring more images and using a faster computer to analyze those images may reduce the detection limit and improve the measurement speed at the same time.

Preferably, the method of the present invention takes less than 1 hour to provide qualitative or quantitative data on a platelet or red blood cell-containing sample. More preferably, the method of the present invention takes less than 30 minutes to provide qualitative or quantitative date on the platelet or red blood cell-containing sample. Further, the method of the present invention takes 15 minutes or less when the steps of lysing a substantial portion of the platelets in the sample and staining the bacteria using a membrane-permeable nucleic acid stain are carried out simultaneously. The invention will be further illustrated by the example given below.

EXAMPLE

A bag of leukocyte-reduced platelets was obtained and stored at room temperature with rocking for a period of five days. On day 2 and each subsequent day, one ml of platelets was removed aseptically from the bag for use in that particular day's measurements.

Bacteria *Escherichia coli* (M65-2) and *Staphylococcus epidermidis* were grown overnight in Luria Broth. The overnight growths were washed by pelletting and resuspending in sterile deionized water three times. Bacterial concentrations in the final suspensions were between $1 \times 10^9$ and $3 \times 10^9$ CFU/ml as determined by microscopic direct counts at 1000× magnification and verified by dilution plate counts.

At the start of each measurement, 40 $\mu$l of one of the bacterial suspensions, 80 $\mu$l of 10% Triton X-100 prepared with sterile deionized water, and 1 $\mu$l of SYTO 13 (the SYTO 13 dye has a concentration of 2 mM in DMSO) were added to 360:1 of the platelet suspension to produce a bacterial concentration near $10^3$, $10^4$, or $10^5$ CFU/ml. The mixture was then mixed thoroughly and incubated at 37° C. for 15 minutes. 200 $\mu$l of this mixture was then filtered onto a 0.4 $\mu$m pore size membrane filter. After being air dried for about 5 minutes, the membrane filter was mounted between two microscope slides. One hundred images were acquired and analyzed from discrete areas of the membrane filter using an automated epifluorescence microscope in less than 10 minutes and the results were obtained as a number of counts based on the image analysis.

For each type of bacteria at each given concentration, triplicate samples were prepared and triplicate measurements were carried out. Multiple control samples, which were treated identically to the testing samples except that no bacteria were included, were also measured. Such measurements were repeated on twelve different days.

For the *Escherichia coli* samples, with bacterial concentrations between $2.4 \times 10^3$ and $3.5 \times 10^3$ CFU/ml, these measurements on twelve different days gave an average of 13 counts for a concentration of $4.6 \times 10^3$ CFU/ml. The 26 *Escherichia coli* control samples averaged 4.5 counts or $1.5 \times 10^3$ CFU/ml. For the *Staphylococcus epidermidis* samples, with bacterial concentrations between $2.6 \times 10^3$ and $3.9 \times 10^3$ CFU/ml, these measurements on twelve different days gave an average of 11 counts for a concentration of $3.1 \times 10^3$ CFUl/ml. The 28 *Staphylococcus epidermidis* control samples averaged 2.4 counts or $8.2 \times 10^2$ CFU/ml. Thus, in this example, the present invention exhibited a detection limit, chosen as 3 times the control average, as low as $3.0 \times 10^3$ CFU/ml, which is a very good result as compared with existing methods which take far longer to be carried out.

In addition to qualitative determination of the existence of bacterial contamination in a platelet-containing sample, the method of the present invention can also be used to quantify the bacterial concentration in the platelet-containing sample. Typically, a series of standard samples having known bacteria concentrations can be prepared using the procedure described above and counts for these standard samples can be measured. A calibration curve of counts versus bacteria concentration can be plotted. The calibration curve may then be used to quantitatively determine the concentration of bacteria in a sample using the counts obtained.

The foregoing detailed description of the invention and examples are not intended to limit the scope of the invention in any way. The scope of the invention is to be determined from the claims appended hereto.

We claim:

1. A method for determining a presence of bacteria in a sample containing platelets comprising the steps of:
    lysing a substantial portion of the platelets in the sample;
    staining the bacteria using a membrane-permeable nucleic acid stain;
    filtering the sample using a membrane filter to retain a material containing stained bacteria on the filter; and
    analyzing the material using epifluorescence microscopy to determine the presence of bacteria in the sample.

2. The method as claimed in claim 1, wherein the step of lysing the platelets is carried out by contacting the platelets with a suitable amount of a suitable lytic agent for a sufficient period of time to lyse 90% of the platelets.

3. The method as claimed in claim 1, wherein the step of lysing the platelets is carried out by contacting the platelets with a suitable amount of a suitable lytic agent for a sufficient period of time to lyse 99% of the platelets while lysing less than 20% of the bacteria in the sample.

4. The method as claimed in claim 3, wherein the suitable amount of the lytic agent ranges from about 0.5% to about 20% of the platelets by volume, and the lytic agent is a detergent.

5. The method as claimed in claim 1, wherein the step of analyzing the material further comprises the steps of:
    acquiring digital images of the material;
    analyzing the digital images to determine a count of the bacteria; and
    comparing the count of the bacteria with a threshold count to ascertain the presence of bacteria.

6. The method as claimed in claim 1, wherein the membrane-permeable nucleic acid stain comprises a low molecular weight cyanine dye.

7. The method as claimed in claim 1, wherein the membrane-permeable nucleic acid stain is a low molecular weight cyanine dye and the lytic agent is a nonionic surfactant based on ethoxylate polymers.

8. The method as claimed in claim 1, wherein the step of staining the bacteria comprises the step of contacting the sample with the membrane-permeable nucleic acid stain for about 2 to about 15 minutes.

9. The method as claimed in claim 1, wherein the membrane filter has a pore size between about 0.2 $\mu$m and about a diameter of a bacteria cell.

10. The method as claimed in claim 1, wherein a material containing substantially all of the stained bacteria is retained on the membrane filter after the filtering step, and wherein the method further comprises the step of drying the material retained on the membrane filter after the sample has been filtered through the membrane filter.

11. A method for determining a concentration of bacteria in a sample containing platelets, comprising the steps of:
    lysing a substantial portion of the platelets without destroying a substantial amount of bacterial cells in the sample;
    staining the bacteria using a membrane-permeable nucleic acid stain;
    filtering the sample using a membrane filter to retain a material containing substantially all of the stained bacteria on the filter; and
    analyzing the material using epifluorescence microscopy and digital image acquisition and analysis to determine the concentration of the bacteria in the sample.

12. The method as claimed in claim 11, wherein the step of analyzing the material further comprises the steps of:
    acquiring digital images of the material;
    analyzing the digital images to determine a count of the bacteria; and
    comparing the count of the bacteria with a calibration curve to determine the concentration of the bacteria.

13. The method as claimed in claim 11, wherein a material containing substantially all of the stained bacteria is retained on the membrane filter after the filtering step, and wherein the method further comprises the step of drying the material retained on the membrane filter after the sample is filtered through the membrane filter.

14. A method for ascertaining a presence of bacteria in a platelet suspension having platelets comprising the steps of:

lysing a substantial portion of the platelets without destroying a substantial amount of the bacteria in the platelet suspension;

staining the bacteria using a membrane-permeable nucleic acid stain;

filtering the platelet suspension using a membrane filter with a suitable pore size, to retain a material containing substantially all of the stained bacteria on the filter; and analyzing the material using epifluorescence microscopy digital image acquisition and analysis to determine the presence of the bacteria in the platelet suspension.

15. The method as claimed in claim 14, wherein the step of lysing the platelets is carried out by contacting the platelet suspension with a sufficient amount of a lytic agent.

16. The method as claimed in claim 15, wherein the amount of the lytic agent ranges from about 0.5% to about 20% of the platelet suspension.

17. The method as claimed in claim 15, wherein the lytic agent is a detergent.

18. The method as claimed in claim 15, wherein the membrane-permeable nucleic acid stain is a low molecular weight cyanine dye and the lytic agent is a nonionic surfactant based on ethoxylate polymers.

19. The method as claimed in claim 14, wherein the step of analyzing the material further comprises the steps of:

acquiring digital images of the material using an automated epifluorescence microscope;

analyzing the digital images using an image analysis program to determine a count of the bacteria; and comparing the count of the bacteria with a threshold count to determine the presence of the bacteria in the platelet suspension.

20. The method as claimed in claim 14 further comprising the step of drying the material retained on the membrane filter after the platelet suspension has been filtered through the membrane filter.

21. A method for determining a presence of bacteria in a sample containing red blood cells comprising the steps of:

lysing a substantial portion of the red blood cells in the sample;

staining the bacteria using a membrane permeable nucleic acid stain;

filtering the sample using a membrane filter to retain a material containing stained bacteria on the filter; and analyzing the material using epifluorescence microscopy to determine the presence of bacteria in the sample.

22. The method as claimed in claim 21, wherein the step of lysing the red blood cells is carried out by contacting the red blood cells with a suitable amount of a suitable lytic agent for a sufficient period of time to lyse at least 90% of the red blood cells.

23. The method as claimed in claim 21, wherein the step of lysing the red blood cells is carried out by contacting the red blood cells with a suitable amount of a suitable lytic agent for a sufficient period of time to lyse at least 99% of the red blood cells while lysing less than 20% of the bacteria in the sample.

24. The method as claimed in claim 21, wherein the step of analyzing the material further comprises the steps of:

acquiring digital images of the material;

analyzing the digital images to determine a count of the bacteria; and comparing the count of the bacteria with a threshold count to ascertain the presence of bacteria.

25. The method as claimed in claim 21, wherein the membrane-permeable nucleic acid stain is a low molecular weight cyanine dye and the lytic agent is a nonionic surfactant based on ethoxylate polymers.

* * * * *